(12) United States Patent
Stanfield et al.

(10) Patent No.: US 10,413,705 B2
(45) Date of Patent: Sep. 17, 2019

(54) CANNULA RING AND RELATED SYSTEMS AND METHODS

(71) Applicant: World Heart Corporation, Salt Lake City, UT (US)

(72) Inventors: Ryan Stanfield, Salt Lake City, UT (US); John Woodard, Salt Lake City, UT (US); Gill Bearnson, Salt Lake City, UT (US)

(73) Assignee: World Heart Corporation, Miami Lakes, FL (US)

( * ) Notice: Subject to any disclaimer, the term of this patent is extended or adjusted under 35 U.S.C. 154(b) by 369 days.

(21) Appl. No.: 13/708,616

(22) Filed: Dec. 7, 2012

(65) Prior Publication Data

US 2013/0150654 A1 Jun. 13, 2013

Related U.S. Application Data

(60) Provisional application No. 61/567,973, filed on Dec. 7, 2011.

(51) Int. Cl.
*A61M 1/10* (2006.01)
*A61M 25/04* (2006.01)
(Continued)

(52) U.S. Cl.
CPC ......... *A61M 25/04* (2013.01); *A61B 17/3421* (2013.01); *A61B 17/3423* (2013.01); *A61M 1/10* (2013.01); *A61M 1/1008* (2014.02); *A61B 17/3462* (2013.01); *A61B 17/3498* (2013.01); *A61B 2017/00867* (2013.01); *A61B 2017/00871* (2013.01); *A61B 2017/347* (2013.01); *A61B 2017/3425* (2013.01); *A61B 2017/3484* (2013.01); *A61B 2017/3488* (2013.01); *A61M 1/12* (2013.01)

(58) Field of Classification Search
CPC ....................................................... A61M 1/10
USPC ................... 623/1.26, 1.15; 600/16; 604/175
See application file for complete search history.

(56) References Cited

U.S. PATENT DOCUMENTS

| 6,017,355 A | 1/2000 | Hessel et al. |
| 6,350,277 B1 * | 2/2002 | Kocur .......................... 623/1.11 |

(Continued)

FOREIGN PATENT DOCUMENTS

CN 1909848 A 2/2007

OTHER PUBLICATIONS

State Intellectual Property Office of the People's Republic of China (SIPO), The Second Notification of Reexamination, dated Dec. 27, 2017, for corresponding Application No. 201280069069.9.

*Primary Examiner* — Matthew W Schall
(74) *Attorney, Agent, or Firm* — Christopher & Weisberg, P.A.

(57) ABSTRACT

Cannula devices and related methods are provided. In accordance with one embodiment, a cannula ring includes a body portion having a substantially cylindrical member defining an opening therethrough. A plurality of anchor arms coupled with the body portion and configured to be positioned in a first, collapsed state and a second, deployed state, wherein the anchor arms each include a free end that is radially displaced from the body portion while in the second, deployed state relative to their positions while in the first, collapsed state. Suture rings and other associated structures and devices are also described.

17 Claims, 13 Drawing Sheets

(51) Int. Cl.
*A61B 17/34* (2006.01)
*A61B 17/00* (2006.01)
*A61M 1/12* (2006.01)

(56) References Cited

U.S. PATENT DOCUMENTS

| | | |
|---|---|---|
| 2003/0163147 A1 | 8/2003 | Rabiner et al. |
| 2004/0127913 A1 | 7/2004 | Voss |
| 2007/0043380 A1 | 2/2007 | Ortiz et al. |
| 2008/0009891 A1 | 1/2008 | Cohn |
| 2008/0255660 A1* | 10/2008 | Guyenot et al. ............ 623/2.14 |
| 2009/0005863 A1* | 1/2009 | Goetz et al. ................ 623/2.18 |
| 2009/0023975 A1* | 1/2009 | Marseille ........... A61B 17/3421 600/16 |
| 2010/0152748 A1 | 6/2010 | Penner et al. |
| 2010/0249491 A1 | 9/2010 | Farnan et al. |
| 2011/0130619 A1 | 6/2011 | Whisenant et al. |
| 2011/0190707 A1 | 8/2011 | Farnan |
| 2012/0010455 A1* | 1/2012 | Reichenbach et al. ......... 600/16 |
| 2012/0143141 A1 | 6/2012 | Verkaik et al. |

\* cited by examiner

CANNULA RING AND RELATED SYSTEMS AND METHODS

CROSS-REFERENCE TO RELATED APPLICATIONS

This application claims the benefit of U.S. Provisional Patent Application 61/567,973, entitled CANNULA RING AND RELATED SYSTEMS AND METHODS, filed on Dec. 7, 2011, the disclosure of which is incorporated by reference herein, in its entirety.

TECHNICAL FIELD

Exemplary embodiments relate to a device for coupling a conduit to a vessel of the human body, and, more particularly to a cannula ring that enables attachment of various devices or structure with a chamber of the heart or other vessel.

BACKGROUND

Mechanical circulatory devices (MCDs) such as artificial hearts, ventricular assist devices (VADs) and other blood circulating systems and components have become increasingly recognized as life saving devices for patients whose hearts are diseased or have been injured by trauma, heart attack or other causes. VADs in particular, are recognized as a major life saving modality for assisting patients who suffer from congestive heart failure.

VADs must be physically connected to the natural heart of patients. In order to connect a VAD to the heart of a patient, a conduit assembly is used. The conduit assembly conventionally has a tubular tip body that is inserted into the heart. For proper functioning, the tip body typically penetrates the heart wall to make a fluid connection with the heart (e.g., with a ventricle of the heart) through the heart wall. However, various difficulties may present themselves in connecting a conduit assembly with the heart. For example, it is desirable to ensure that there are no leaks through the heart wall in the opening through which the conduit assembly is placed. On the other hand, it is desirable to enable repositioning, removal and possible replacement using minimally invasive techniques.

For these, and a variety of other reasons, there is a continued desire to provide enhanced methods, systems and devices that will improve the functionality and efficiency of VADs and other similar devices.

BRIEF SUMMARY OF THE INVENTION

In accordance with the present invention, various devices, components and methods associated with the cannulation of a tissue structure are set forth. In accordance with one embodiment, a cannula ring is provided. The cannula ring includes a body portion having a substantially cylindrical member defining an opening therethrough. A plurality of anchor arms are coupled with the body portion and configured to be positioned in a first, collapsed state and a second, deployed state. The anchor arms each include a free end that is radially displaced from the body portion while in the second, deployed state relative to their positions while in the first, collapsed state. In one embodiment, a coupling structure is associated with the body portion and the body portion may include a surface feature configured to engage abutting tissue.

In one embodiment the anchor arms extend substantially axially along the body portion while in the first, collapsed state. In another embodiment the anchor arms extend substantially circumferentially about the body portion while in the first, collapsed state. The anchor arms may be formed of a shape memory material. In one embodiment, each anchor arm includes a wire structure. In one embodiment a portion of each anchor arm is integrally formed with the body portion.

In accordance with another embodiment, a cannula device comprises a first structure having a convex gimbaled surface. The device also includes a suture ring having a body portion and a ring portion. The body portion has a concave gimbaled surface coupled with the convex gimbaled surface of the first structure, wherein the suture ring may pivot in at least two planes relative to the first structure. In various embodiments, the first structure may include a conduit, a blood pump a cannula ring or some other device.

In accordance with another embodiment of the invention, a cannula device is provided that comprises a first structure and a suture ring. The suture ring includes a body portion, a ring portion and a locking mechanism, wherein the suture ring may coupled with the first structure and be selectively locked at a plurality of positions relative to the first structure.

In accordance with another embodiment, a cannula device is provided that comprises a first structure and a suture ring coupled with the first structure. The first structure defines an opening that is eccentrically located relative to a perimeter defined by the suture ring. In one embodiment the perimeter is an outer perimeter of the suture ring. In another embodiment, the perimeter is an inner perimeter of the suture ring.

In accordance with another embodiment of the invention, a suture ring is provided that comprises: a coupling portion having an opening formed therein; a ring portion configured for attachment to a tissue structure; and a valve associated with the coupling portion, the valve being configured to selectively enable or inhibit fluid flow through the opening of the coupling portion.

Other features and advantages may be possible, and it is not necessary to achieve all or any of these features or find any of the stated advantages in any embodiment. Therefore, nothing in the forgoing description can or should be taken as limiting.

BRIEF DESCRIPTION OF THE SEVERAL VIEWS OF THE DRAWINGS

The foregoing and other advantages of the invention will become apparent upon reading the following detailed description and upon reference to the drawings in which.

DETAILED DESCRIPTION OF THE INVENTION

Figure 1A:
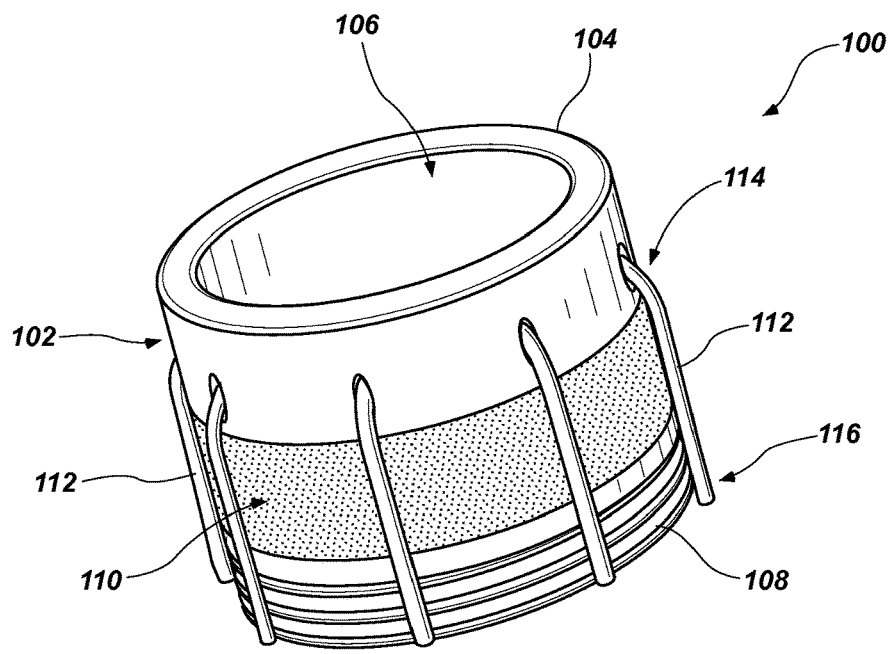
FIGS. 1A and 1B show perspective views a cannula ring in accordance with an embodiment of the present invention.
Figure 1B:
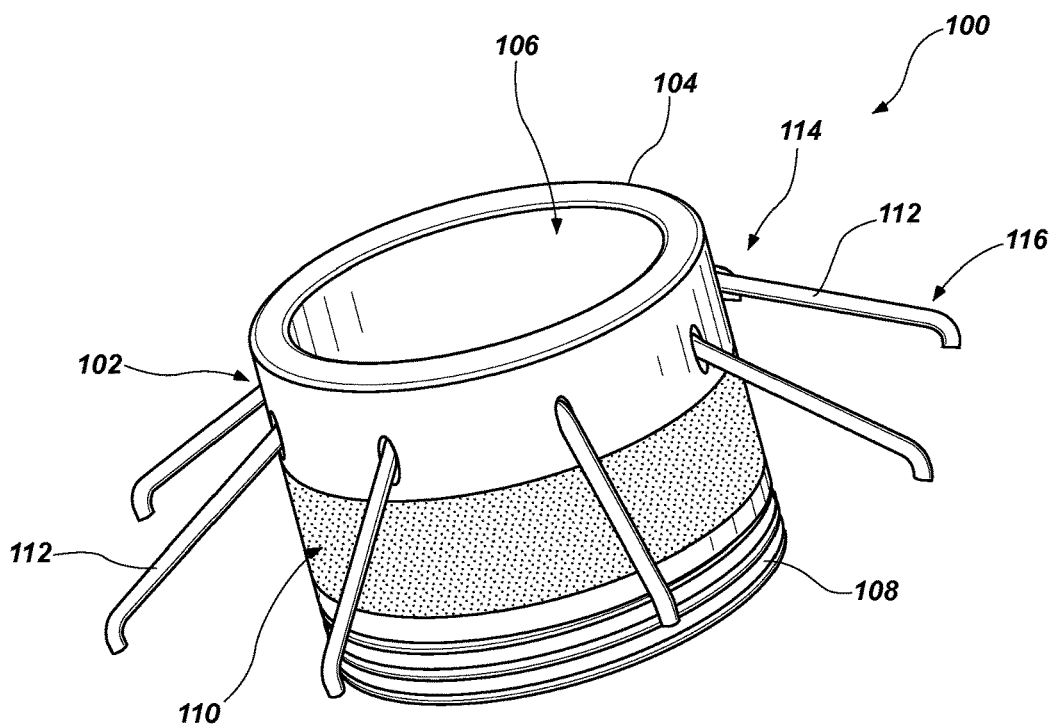

Referring to FIGS. 1A-1B a first embodiment of the cannula ring 100 is shown in a first state (FIG. 1A) and a second state (FIG. 1B). The cannula ring 100 includes a body portion 102 which may be formed of a substantially rigid material such as, for example, a metal, metal alloy, or any of a variety of biocompatible plastic materials. The body portion 102 may be formed generally as a tubular member having a substantially cylindrical wall 104 defining a lumen 106 or an opening passing through the body 102. The body portion 102 may include a number of features including a coupling structure 108 formed at one end of the body portion 102 that is configured to enable coupling with another device or structure such as, for example, a blood pump or a conduit. The coupling structure 108 may include, for example, a plurality of threads, a keyed twist-lock structure, a plurality of shoulders used in association with a ratchet structure, or it may be configured for connection with a compression coupling.

The external surface of the body portion 102, or at least a portion thereof, may also include one or more surface features 110 configured to enhance long term placement of the cannula ring 100 in the body of a patient. For example, a surface feature 110 may include a textured surface that is formed on the body portion 102 at a location that is intended to interact with tissue of a patient—e.g., a wall of the patient's heart. The surface feature 110 may be configured to help maintain the position of the cannula ring 100 when implanted in a patient. In one embodiment, such a surface feature 110 may be configured to engage the tissue and provide a desired level of resistance between the cannula ring 100 and the engaged tissue. In another embodiment, the surface feature may be configured to promote tissue in-growth to the body portion 102 of the cannula ring 100.

The cannula ring 100 also includes a plurality of anchor arms 112 positioned about the perimeter of the body portion 102 in a substantially equally spaced pattern (although other patterns may be used). As shown in FIG. 1A, the anchor arms 112 may be configured to assume a first position wherein they are positioned adjacent to or even abut the body portion 102 of the cannula ring 100. Such a position may be referred to as a collapsed state or position. The anchor arms 112 may be placed in a collapsed state when the cannula ring 100 is being delivered to a site for implantation making the cannula ring 100 more compact and easier to manipulate when positioning and orienting the cannula ring 100 at a site for implanting. As seen in FIG. 1B, the anchor arms 112 may also be configured to assume at least one other position (i.e., other than the collapsed state), which may be referred to as a deployed state or position. While in the deployed state, a portion of the anchor arms 112 may flare out in a radial direction relative to the body portion 102. In the embodiment shown in FIG. 1B, a first end 114 of each anchor arm 112 is coupled with the body portion 102 while a second end 116 of the anchor arms 112 is free and displaceable between the collapsed state (FIG. 1A) and the radially flared or displaced position of the deployed state. Stated another way, the first end 114 and second end 116 of each anchor arm 112 may be at a substantially equal radial distance from a longitudinal axis extending through the lumen 104 while in the collapsed state, while the second end 116 of each anchor arm 112 is displaced radially outward of the first end 114 when in a deployed state.

In one embodiment, the anchor arms 112 may be formed of a metal material. For example, the anchor arms may be formed of a shape memory alloy such as nitinol. In such a case, the anchor arms 112 may be configured to be biased toward the deployed state. For example, referring briefly to FIG. 1C, a restraining structure 120 may be positioned about the anchor arms 112, holding them in the collapsed state, while the cannula ring is being delivered and positioned at a desired location. Once the cannula ring has been placed in a desired position (e.g., through an opening formed in a tissue structure such as the wall of a heart), the restraint structure 120 may be removed from the cannula ring 100 enabling the anchor arms 112 to be displaced to the deployed state. With the anchor arms 112 in the deployed state, the second ends 116 of the anchor arms may be positioned to abut the tissue structure (e.g., the vessel wall) on the distal side of the tissue structure in order to anchor the cannula ring 100 within the opening in which it has been placed. As will be described in further detail below, the body portion 102 may be coupled with another device or component (e.g., a suture ring) to anchor the cannula ring 100 on the proximal side of the tissue structure, working in concert with the anchor arms 112, to fix the cannula ring 100 in a desired position and orientation relative to the tissue structure.

Referring again to FIG. 1C, the restraint structure 120 may include a generally circuitous band 122 that is positioned about the body portion 102 and the anchor arms 112, holding the anchor arms in the collapsed state. A circuitous band 122 may include a tab portion that may be easily grasped by hand or by an appropriate tool. A series of perforations 126 may be provided at a circumferential location that corresponds with the tab 124, the perforations extend along an axial path through the band 122. By applying an appropriate force to the tab 124, the band 122 may be torn through the series of perforations 126 to remove the band from the cannula ring 100 and enable the anchor arms 112 to expand or be displaced to their deployed state (FIG. 1B). In other embodiments, a band or sleeve may be provided about the anchor arms 112 to maintain them in a collapsed state until slid axially, relative to the body portion, a specified distance in order to enable the anchor arms 112 to expand radially once free of the band or sleeve.

Figure 1C:
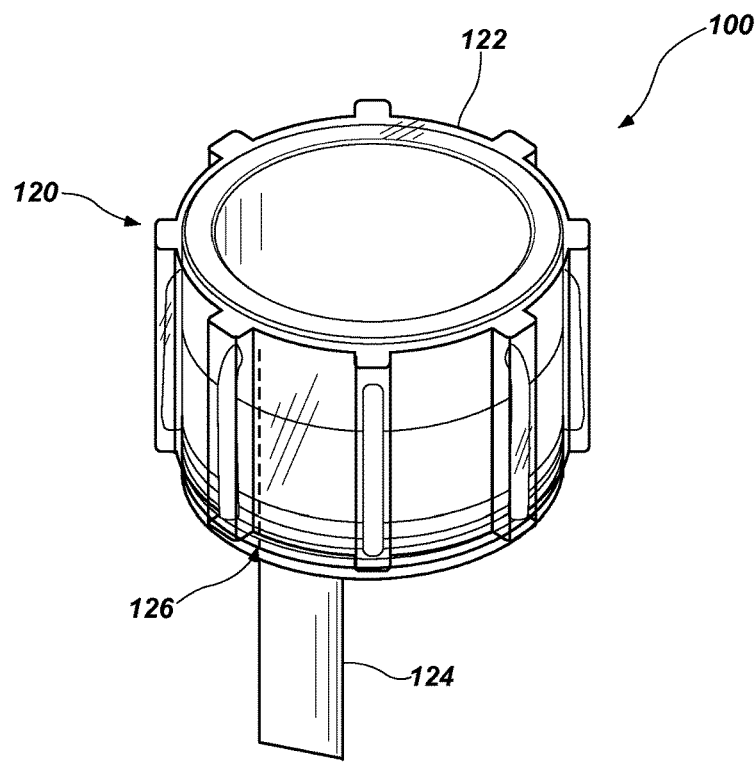
FIG. 1C shows a perspective view of the cannula ring shown in FIGS. 1A and 1B with a component associated with the introduction of the cannula ring into a patient according to an embodiment of the invention.
Figure 1D:
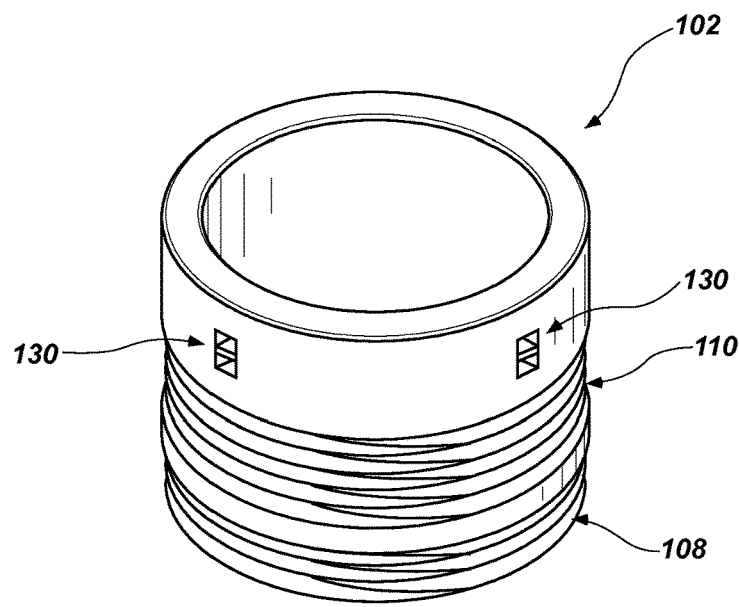
FIG. 1D shows a perspective view of a component of a cannula ring in accordance with another embodiment of the invention.

Referring briefly to FIG. 1D, the body portion 102 of the cannula ring 100 is shown. The body portion 102 is shown without the anchor arms 112 coupled therewith. Openings 130 may be formed in the body portion for coupling of the anchor arms 112 therewith. As previously described, the coupling structure 108 may include threads, ratchet teeth, or other structures for adjustably coupling another component with the body portion 102. Also, as noted above, surface features 110 may be formed on the body portion 102. The surface features 110 shown in FIG. 1D include a knurled surface, but may include some other texture pattern or may include a tissue growth member formed in or coupled with the body portion 102.

It is also noted that the embodiment shown in FIG. 1D includes a patterning of openings 130 for four different anchor arms 112 while the embodiments shown in FIGS. 1A-1C include eight anchor arms 112. The present invention is not limited to any specific number of anchor arms 112 and different embodiments may have a different number depending on a variety of factors including, for example, the size and geometry of the anchor arms as well as the material from which the anchor arms are formed. Additionally, the openings 130 formed in the body portion 102 may be formed as through holes or as blind holes and may include structure configured to help grasp and retain the anchor arms 112 therein.

When implanted in a tissue opening (such as during a cannulation procedure), the cannula ring creates a predictable opening through a tissue structure, such as the wall of a heart, enabling other devices to pass through and access the area on the opposing side of the tissue structure. The cannula ring 100 may be placed using known minimally invasive surgical (MIS) techniques such as, for example, a thoracotomy. The cannula ring 100 may be removed when other components (e.g., blood pumps) are removed, or it may be left in place with a plug or other structure used to prevent any fluid flow through the opening 106.

Figure 2A:
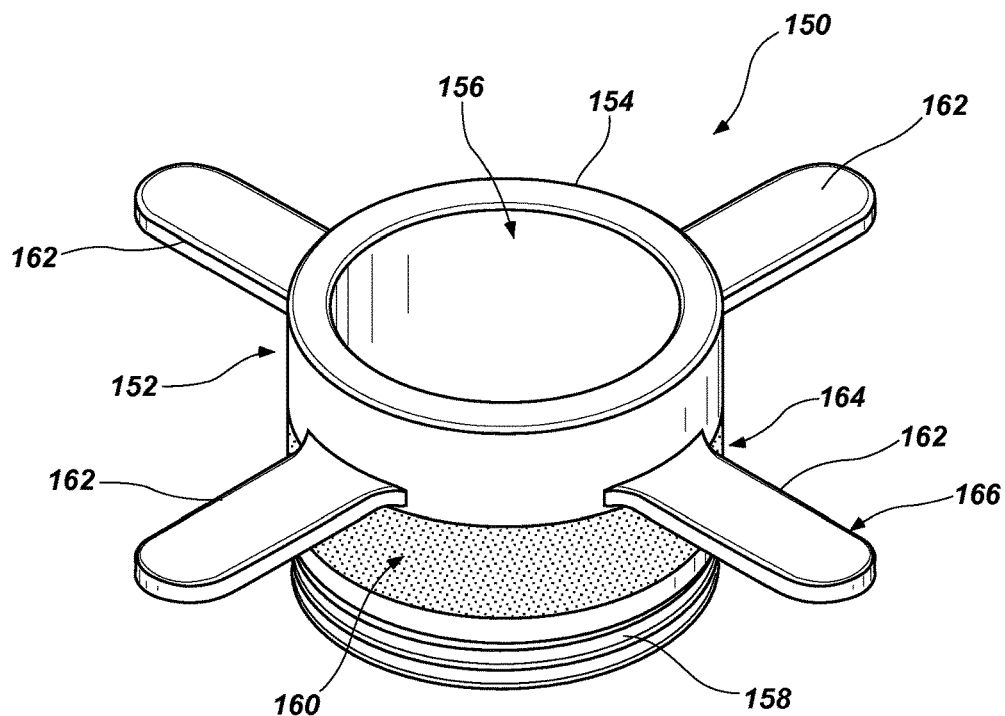
FIGS. 2A and 2B show perspective views a cannula ring in accordance with another embodiment of the present invention.

Referring now to FIG. 2A, a cannula ring 150 is shown in accordance with another embodiment of the invention. The cannula ring includes a body portion 152 which may be formed generally as a tubular member having a substantially cylindrical wall 154 defining a lumen 156 or an opening passing through the body 152. The body portion 152 may include a number of features including, for example, coupling structure 158 formed at one end of the body portion 152 that is configured to enable coupling with another device or structure such as, for example, a blood pump or a conduit. The external surface of the body portion 152, or at least a portion thereof, may also include one or more surface features 160 configured to enhance long term placement of the cannula ring 150 in the body of a patient such as has been described above.

The cannula ring 150 also includes a plurality of anchor arms 162 positioned about the outer perimeter or the outer circumference of the body portion 152. While FIG. 2A shows the anchor arms 162 in a deployed position (similar to the deployed position of the anchor arms 112 shown in FIG. 1B), they may also be placed in a collapsed state or position such as has been described above with respect to the cannula ring 100 shown in FIGS. 1A and 1C. In the embodiment shown in FIG. 2A, the anchor arms 162 are formed of the same material and may be integrally formed with the body portion 152. For example, the anchor arms 162 may be formed as flaps extending from the body portion 152 having a first end 154 coupled to, or integrally formed with, the body portion 152, and a free end 156 radially displaced from the body portion 152 (while in the deployed state). One or more surfaces of the anchor arms 162 may be textured or treated to enhance their interaction with abutting tissue and, in some embodiments, even promote tissue growth.

In one embodiment, the body portion 152 and the anchor arms 162 may be formed of a polymer material. In one particular embodiment, the body portion 152 and the anchor arms may be formed of a shape memory polymer material (sometimes referred to as a smart material). It is noted that with the increased width of the anchor arms 162 relative to anchor arms 112 of cannula ring 100), a reduced number anchor of arms may be used to secure the cannula ring within an opening of a tissue structure. Of course, the present invention is not limited to a particular number of anchor arms in any of the described embodiments.

Figure 2B:
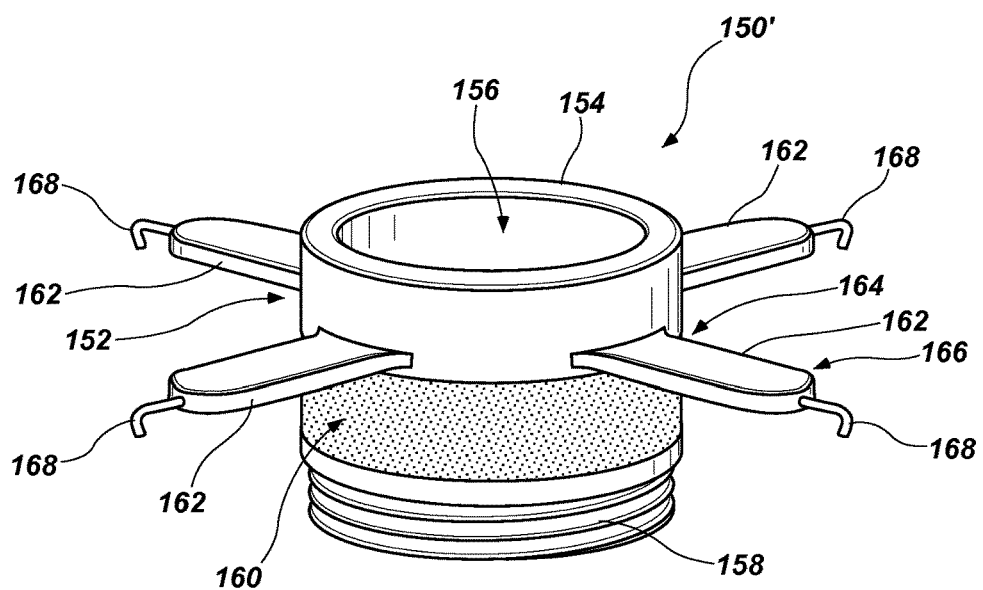

Referring now to FIG. 2B, a cannula ring 150' is shown that is similar to the cannula ring 150 depicted in FIG. 2A. The cannula ring 150' includes a body portion 152 which may be formed generally as a tubular member having a substantially cylindrical wall 154 defining a lumen 156 or an opening passing through the body 152. The body portion 152 may include a number of features including, for example, coupling structure 158 formed at one end of the body portion 152 that is configured to enable coupling with another device and one or more surface features 160 configured to enhance long term placement of the cannula ring 150' in the body of a patient such as has been described above.

The cannula ring 150' also includes a plurality of anchor arms 162 positioned about the outer perimeter or the outer circumference of the body portion 152. The anchor arms 162 are generally similar to those described with respect to FIG. 2A, but additionally include reinforcing structures 168. Thus, FIG. 2B shows a cannula ring 150' having anchor arms that are the combined structures of those shown in FIGS. 1A-1A and FIG. 2A. In other words, the anchor arms 162 include the strut-like structures described with respect to cannula ring 100 (i.e., anchor arms 112 in FIGS. 1A-1C) embedded within the flap-like structures described with respect to cannula ring 150 in FIG. 2A. The anchor arms 162 shown in FIG. 2B may provide enhanced support and resistance to the cannula ring becoming dislodged or displaced after it has been implanted and coupled with other devices. Such additional support may be desired in various circumstances depending on a variety of factors including, for example, the size of the opening, the thickness of the tissue structure into which the cannula ring will be implanted, and the overall integrity of the tissue structure.

Figure 3:
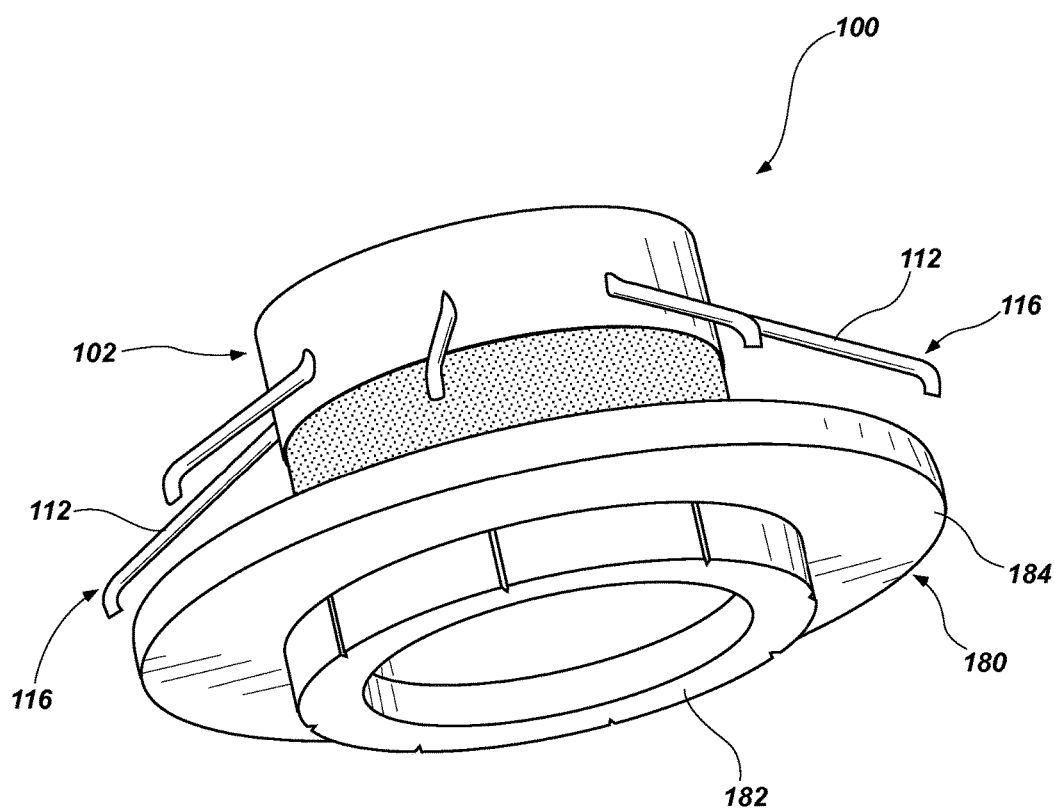
FIG. 3 shows a perspective view of a cannula ring in accordance with yet another embodiment of the invention.

Referring now to FIG. 3, a cannula ring 100 is shown with a suture ring 180 coupled therewith. The suture ring 180 may include a coupling portion 182 that engages with the body portion 102 of the cannula ring 100. Such coupling of the two components may be adjustable or it may be non-adjustable. An adjustable connection between the suture ring 180 and the cannula ring 100 will accommodate variation in the thickness of a tissue structure (e.g., a vessel wall), with the axial position of the suture ring 180 being variable with respect to the axial position of the free ends 116 of the anchor arms 112.

The suture ring 180 includes a ring portion 184 that may include a cloth or fibrous material configured for stapling, suturing or otherwise fastening the suture ring to adjacent tissue. In addition to fastening mechanisms such as sutures or staples (or as an alternative), adhesive may be used to secure the suture ring to adjacent tissue. As discussed above, when positioned within an opening of a tissue structure, the free ends 116 of the anchor arms 112 abut a distal surface of the tissue structure (e.g., the internal surface of a ventricle) while the suture ring 180 (or some other coupling device) abuts the proximal surface of a tissue structure (e.g., the external surface of a heart) to secure the cannula ring 100 in a desired position.

Figure 4A:
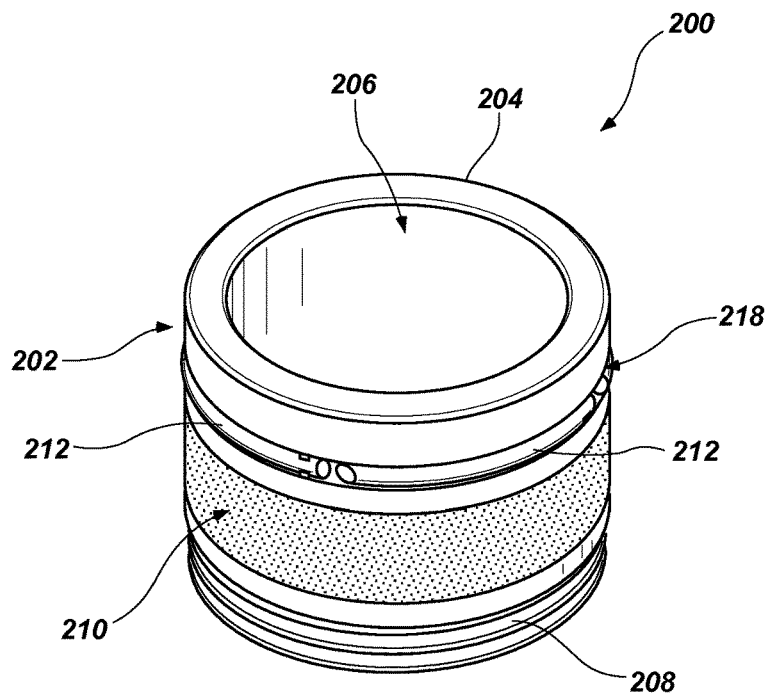
FIGS. 4A and 4B show perspective views a cannula ring in accordance with another embodiment of the present invention.
Figure 4B:
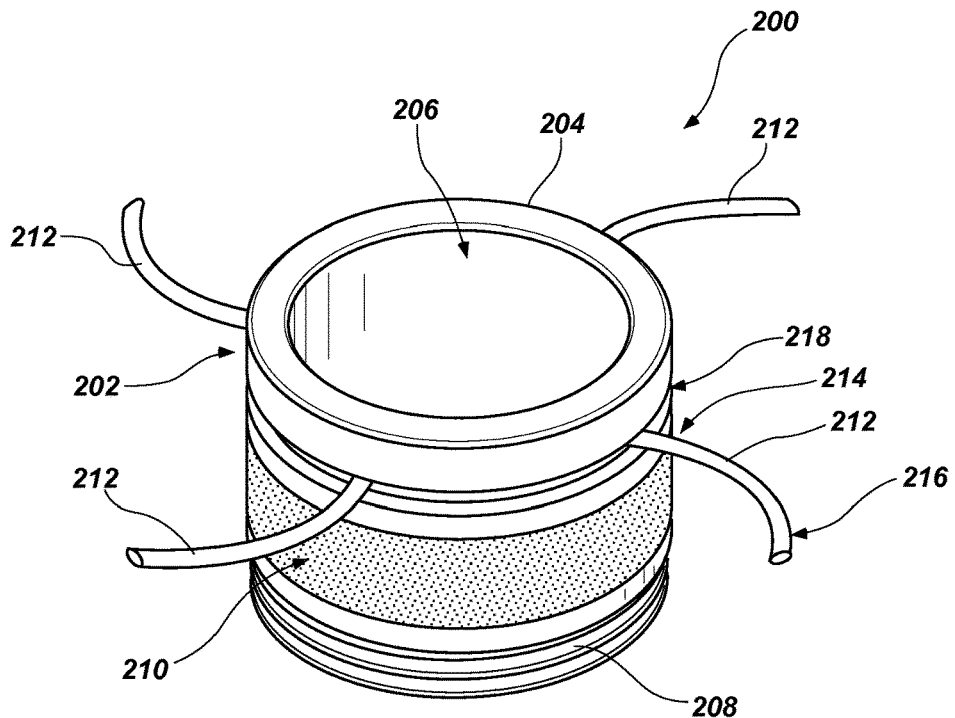

Referring now to FIGS. 4A and 4B, a cannula ring 200 is shown in accordance with another embodiment. The cannula ring 200 includes a body portion 202 which may be formed generally as a tubular member having a substantially cylindrical wall 204 defining a lumen 206 or an opening passing through the body 202. The body portion 202 may include a number of features including, for example, coupling structure 208 formed at one end of the body portion 202 that is configured to enable coupling with another device or structure such as described above. The coupling structure 208 may include, for example, a plurality of threads, a keyed twist-lock structure, a plurality of shoulder used in association with a ratchet structure, or it may be configured for connection with a compression coupling.

The external surface of the body portion 202, or at least a portion thereof, may also include one or more surface features 210 configured to enhance long term placement of the cannula ring 200 in the body of a patient such as described above. The cannula ring 200 also includes a plurality of anchor arms 212 positioned about the perimeter of the body portion 202. As shown in FIG. 4A, the anchor arms 212 may be configured to assume a first position where they are positioned circumferentially adjacent to, and may abut, the body portion 102 of the cannula ring 100. In one embodiment, as seen in FIG. 4A, the anchor arms 212 may be disposed within a circumferential groove 218 formed in an outer surface of the body portion 202. Such a position may be referred to as a collapsed state or position. The anchor arms 212 may be placed in a collapsed state when the cannula ring 100 is being delivered to a site for implantation making the cannula ring 100 more compact and easier to manipulate and position at a site for implanting. As seen in FIG. 4B, the anchor arms 112 may also be configured to assume at least one other position (i.e., other than the collapsed state), which may be referred to as a deployed state or position. While in the deployed state, a portion of the anchor arms 212 flare out in a radial direction relative to the body portion 202. In the embodiment shown in FIG. 4B, a first end 214 of each anchor arm 212 is coupled with the body portion 202 while a second end 216 of the anchor arms 212 is free and is displaceable between the collapsed state (FIG. 1A) and the radially flared or displaced position of the deployed state. The anchor arms 212 extend from the circumference of the body portion 202 in a spiral-type pattern such that they all lie in a substantially common radial plane.

In one embodiment, the anchor arms 212 may be formed of a metal material. For example, the anchor arms may be formed of a shape memory alloy such as nitinol. In such a case, the anchor arms 212 may be configured to be biased toward the deployed state such as has been described with respect to other embodiments. Once the cannula ring 200 has been placed in a desired position (e.g., through an opening formed in a tissue structure such as the wall of a heart), the anchor arms 212 may be displaced to the deployed state. In one embodiment, with the anchor arms 212 in the deployed state, the anchor arms 212 may be positioned to abut the tissue structure (e.g., the vessel wall) on the distal side of the tissue structure in order to anchor the cannula ring 200 within the opening in which it has been placed. In such an embodiment, the anchor arms 212 may be configured so that a substantial portion of the length of each arm (e.g., a majority of the length or more) may be in contact with tissue on the distal side of the tissue structure. In another embodiment, the anchor arms may be displaced from the collapsed state while they are positioned between a distal surface and a proximal surface of the tissue structure so that they engage a perimeter surface of the opening within the tissue structure. If desired, the cannula ring 200 could then be rotated causing the anchor arms to engage and embed themselves in the tissue structure. As previously described, the body portion 202 may be coupled with another device or component to anchor the cannula ring 200 on the proximal side of the tissue structure, working in concert with the anchor arms 212, to fix the cannula ring 200 in a desired position and orientation relative to the tissue structure.

Figure 5A:
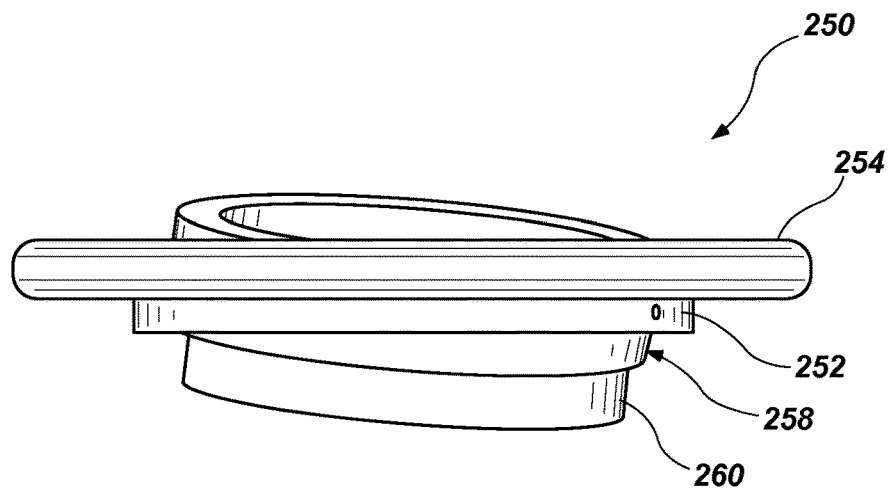
FIGS. 5A and 5B show a perspective view, and a cross-sectional view, respectively, of a cannula ring in accordance with another embodiment of the invention.
Figure 5B:
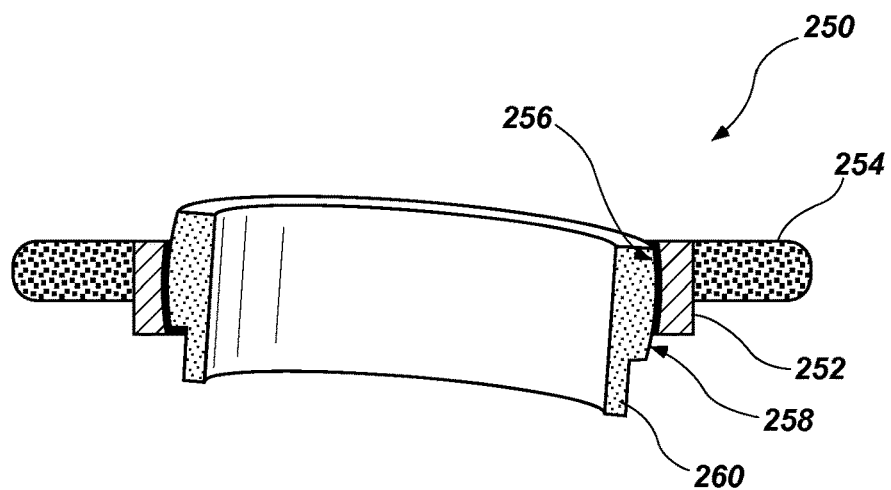

Referring now to FIGS. 5A and 5B, a suture ring 250 is shown in accordance with another embodiment of the present invention. The suture ring includes a coupling portion 252 that engages another structure, generically referred to herein as a cannula structure 260. The cannula structure 260 may include, for example, the body portion of a cannula ring, an engagement sleeve (e.g., a compression sleeve or other coupling structure) for engagement with the body portion of the cannula ring, or it may include other structures associated with a cannula device, a blood pump or some other fluid flow device. The suture ring 250 also includes a ring portion 254 that may be configured such as described above with respect to other suture rings.

The coupling portion 252 includes a concave gimbaled surface 256 that matingly engages a convex gimbaled surface 258 of the cannula structure 260. The gimbaled surfaces 256 and 258 may be substantially spherical, meaning that they include a portion of a sphere, such as a sphere that has been truncated on both sides of an equatorial line. The gimbaled coupling of the coupling portion 252 with the cannula structure 260 enables the coupling portion 252 and the ring portion 254 to pivot in multiple planes relative to cannula structure 260. Such a configuration enables the suture ring 250 to accommodate the variations of anatomy that will be encountered when implanting, for example, a cannula ring in a tissue structure such as the wall of a heart (e.g., to access a ventricle). Additionally, a gimbaled configuration enables the hole or opening that is to be formed in a tissue structure to be located in a greater variety of places while being able to still provide a secure and leak-free connection.

Figure 6A:
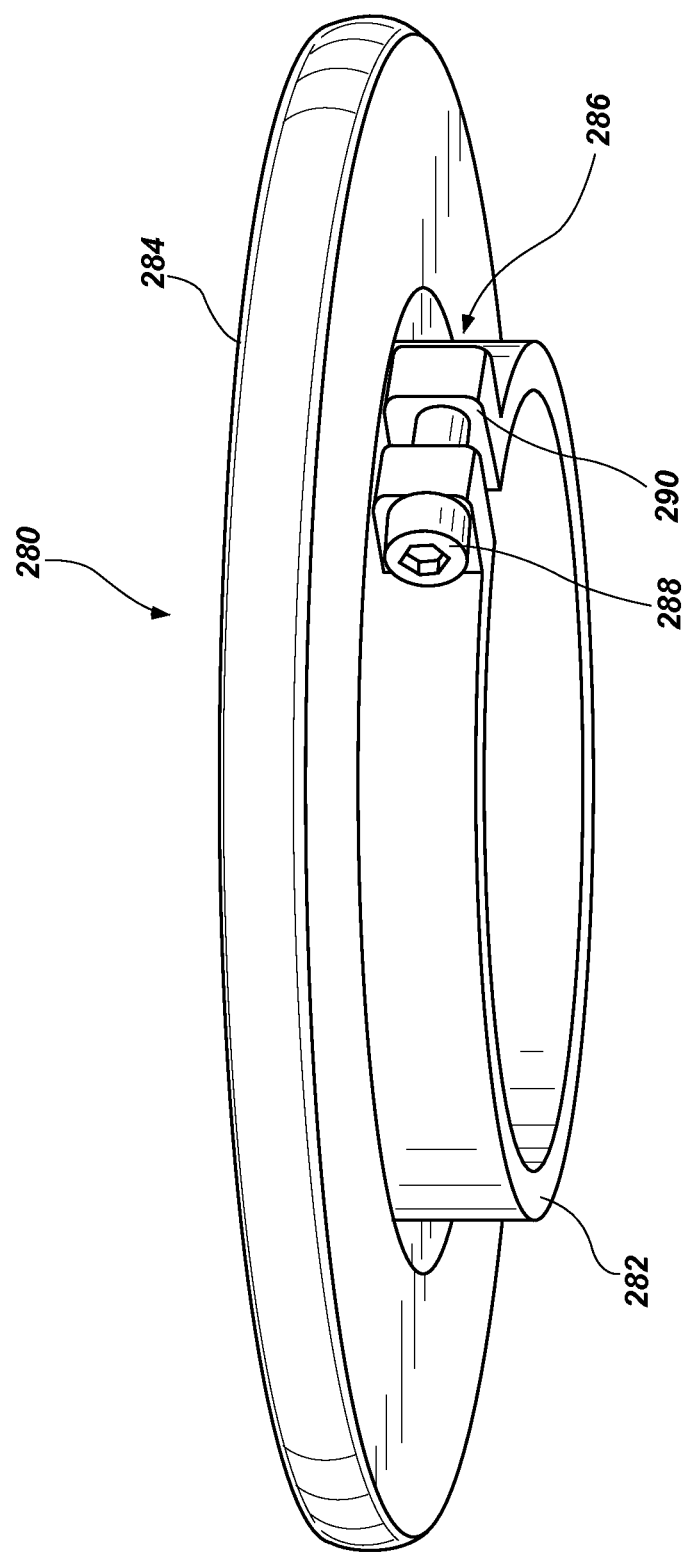
FIGS. 6A-6D show various views of a cannula ring, and other components, in accordance with an embodiment of the present invention.
Figure 6B:
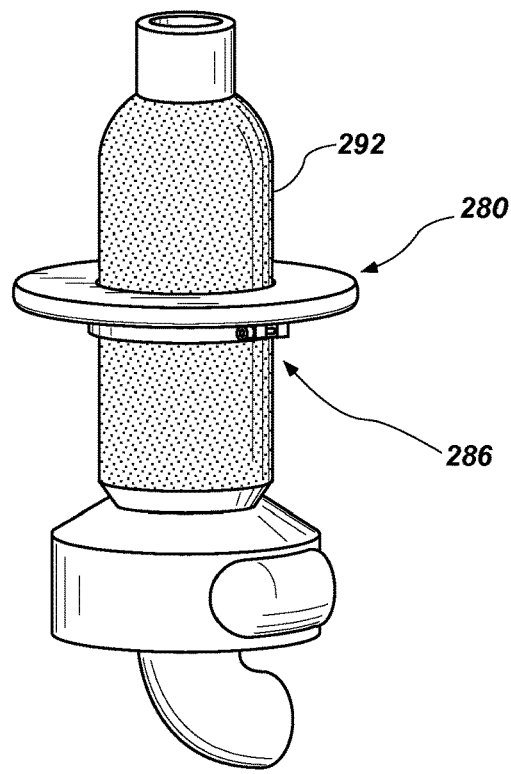
Figure 6C:
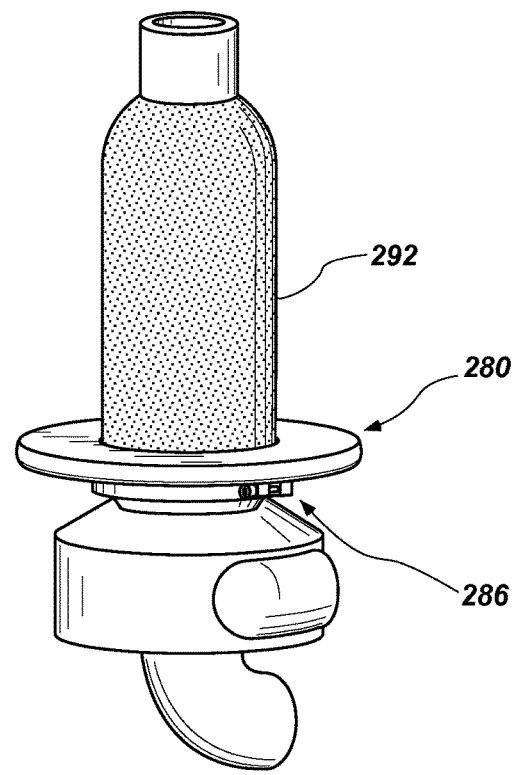
Figure 6D:
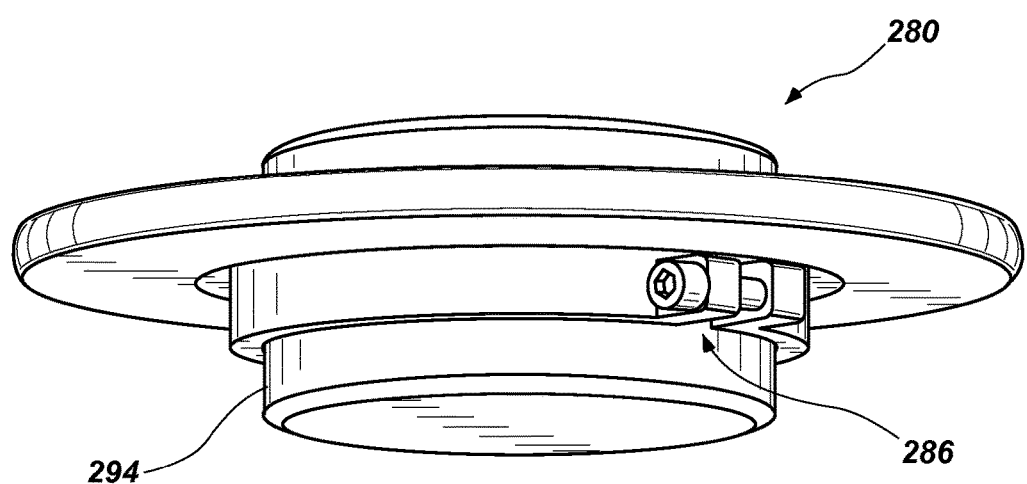

Referring to FIGS. 6A-6D, another suture ring 280 is shown in accordance with an embodiment of the present invention. The suture ring 280 includes a coupling portion 282 configured to couple with a cannula structure (e.g., a cannula ring, an engagement sleeve, or other structures or devices) and a ring portion 284 configured for attachment with adjacent tissue. The cannula ring 280 further includes a locking mechanism 286. In one embodiment, the locking mechanism 286 includes a set screw 288 associated with a split ring 290 (which may formed in conjunction with the coupling portion 282 as shown in FIG. 6A). The set screw enables the tightening and loosening of the split ring 290 so that the suture ring 280 may be secured in a desired position, loosened and repositioned (if desired), and then secured again. Thus, as shown in FIGS. 6B and 6C, the suture ring 280 may be secured at a first position on a cannula structure 292 (shown as an intraventricular pump—see FIG. 6B) and then repositioned and secured at its new position (see FIG. 6C). Such a configuration provides securement of the suture ring 280, regardless of its position relative to the associate cannula structure 292, and accommodates variation in tissue thickness as well as the ability to adjust depending, for example, the position and orientation of related components coupled to the cannula structure 292. The use of an adjustable, locking mechanism 286 also enables the removal and insertion of various components through the ring portion 282 of the suture ring 280. For example, referring briefly to FIG. 6D, while implanting or explanting a cannula structure 292, it may be desirable to place a plug 294 within the ring portion and lock it into place, thereby preventing fluid flow while the cannula structure 292 or other components are absent (e.g., are being prepared for implant or have been explanted).

It is noted that the locking mechanism of suture ring 280 and the gimbaled configuration of suture ring 250 (FIGS. 5A and 5B) may be combined in a single suture ring to provide further adjustability.

Figure 7A:
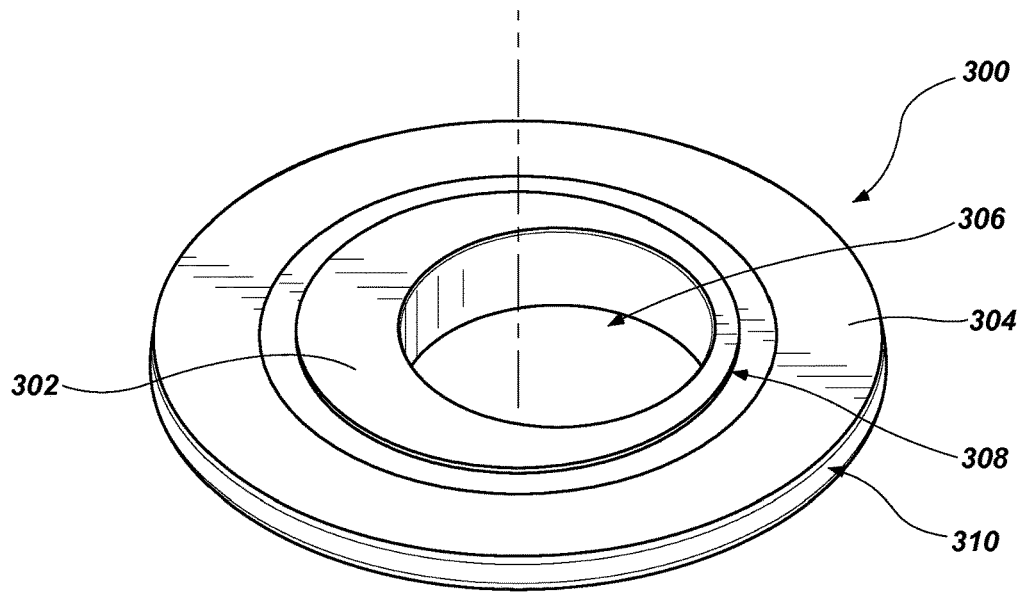
FIGS. 7A and 7B show perspective views of a cannula ring in accordance with a further embodiment of the invention.
Figure 7B:
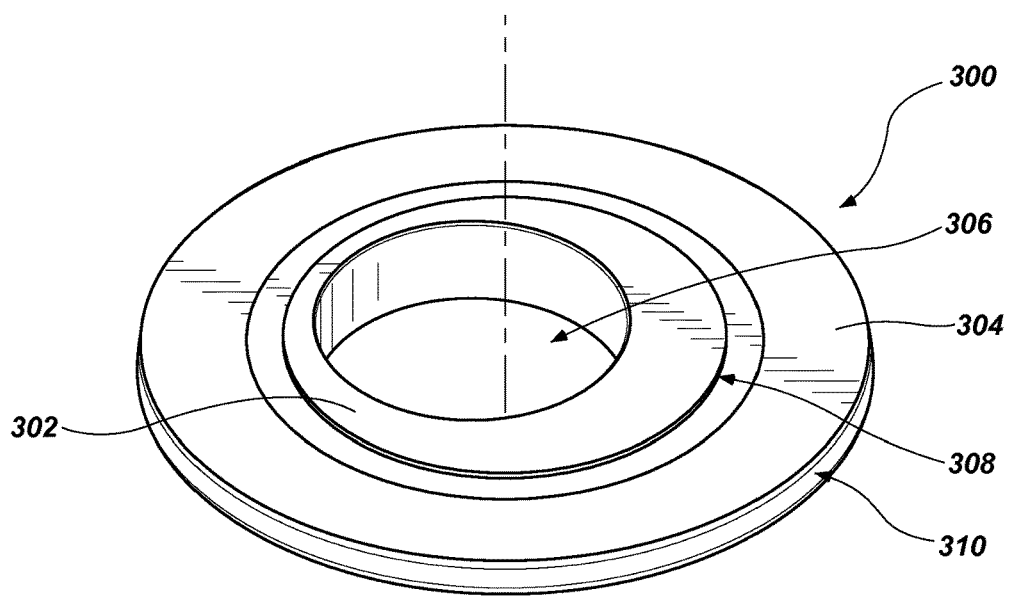

Referring now to FIGS. 7A and 7B, another suture ring 300 is shown in accordance with an embodiment of the present invention. The suture ring 300 includes a coupling portion 302 and a ring portion 304 such as has been described above in various embodiments. An opening 306 in the coupling portion 302 is positioned eccentrically relative to either, or both, of an inner perimeter 308 of the ring portion 304 and an outer perimeter 310 of the ring portion 304. In the embodiment shown in FIGS. 7A and 7B, the opening 306 is eccentrically located relative to both of the circular perimeters of the ring portion 304. The eccentricity of the opening 306 enables the suture ring 300 to be rotated, relative to an opening in a tissue structure, and relative to a cannula structure or other device that may be positioned through an opening in a tissue structure, to accommodate variations in the specific anatomy encountered by a practitioner during implant of a device. Thus, depending on the conditions encountered, the suture ring 300 may be oriented with the opening 306 offset to the right, as shown in FIG. 7A, with the opening 306 offset to the left, as shown in FIG. 7B, or in some different orientation as may be required.

As with other embodiments, the eccentricity of the opening is not limited to the embodiments shown in FIGS. 7A and 7B, but may be combined with other features, other components and other embodiments described herein.

Figure 8A:
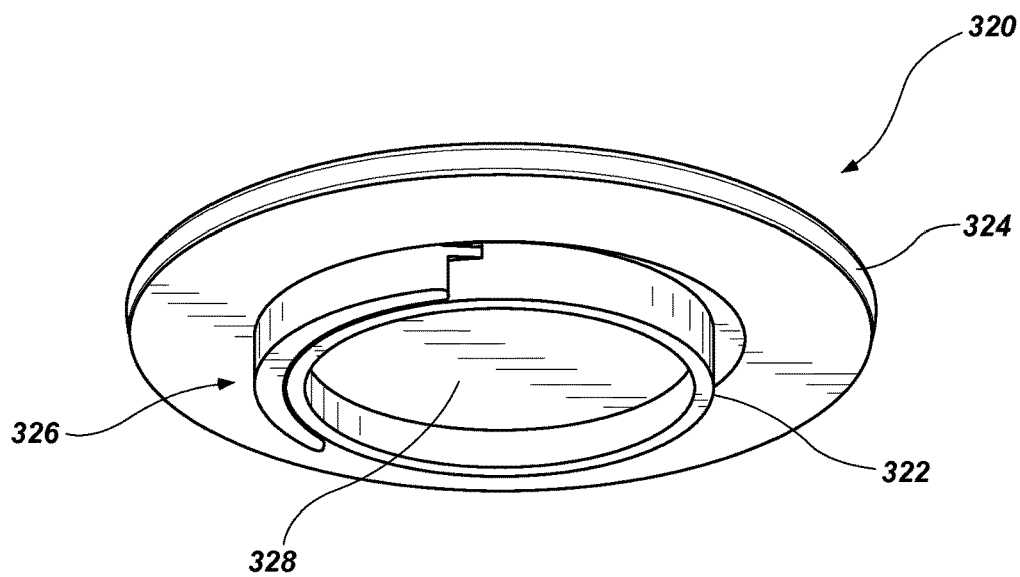
FIGS. 8A and 8B show perspective views of a cannula ring in accordance with another embodiment of the present invention.
Figure 8B:
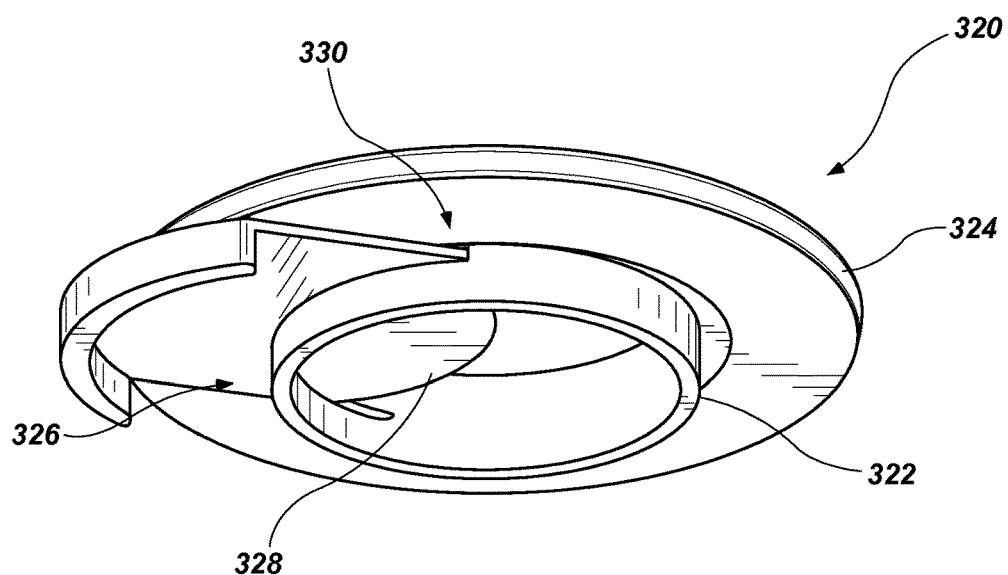

Referring now to FIGS. 8A and 8B, another suture ring 320 is shown in accordance with an embodiment of the present invention. The suture ring 320 includes a coupling portion 322 and a ring portion 324 such as described above with respect to other embodiments. Additionally, the suture ring 320 includes a valve 326 associated with the coupling portion 302 to enable selective fluid flow through the ring portion 322. For example, with the suture ring coupled to an implanted cannula ring (e.g., cannula ring 100), it may be desirable to prevent fluid flow through the cannula ring prior to coupling the cannula ring with another device (e.g., a blood pump). Thus, the valve 326 may be placed in a closed position (see FIG. 8A) until the various components are connected, at which time, the valve 326 may be opened (see FIG. 8B) to enable fluid flow. As shown in FIGS. 8A and 8B, the valve 326 may be configured as a simple gate valve with a gate or partition 328 that slides in a substantially linear direction through a slot 330 formed in the coupling portion 322. While not specifically shown, a locking mechanism may also be incorporated to maintain the gate 328 in one or more desired positions relative to the coupling portion 322 (e.g., closed, open, partially opened). Additionally, the valve may include seals, or be so constructed, to maintain a fluid tight barrier when in the closed position.

Figure 9A:
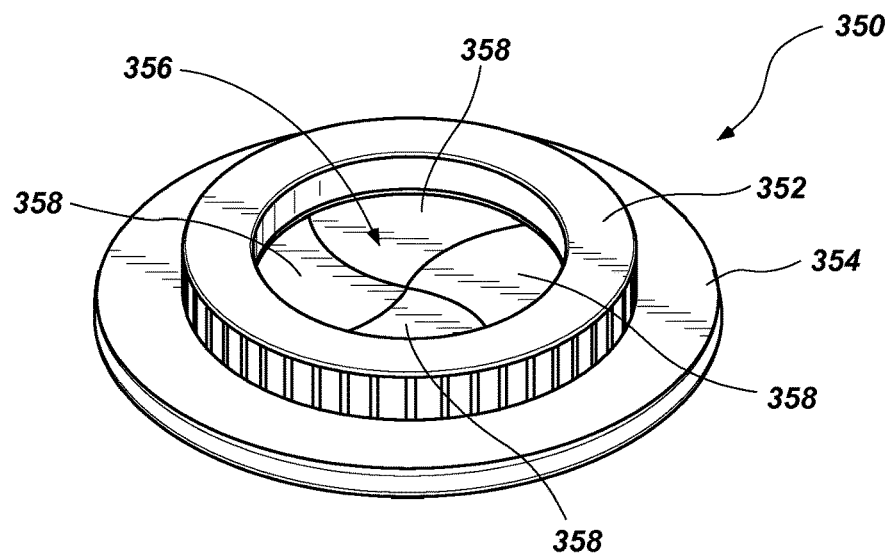
FIGS. 9A and 9B show perspective views of a cannula ring in accordance with yet a further embodiment of the invention.
Figure 9B:
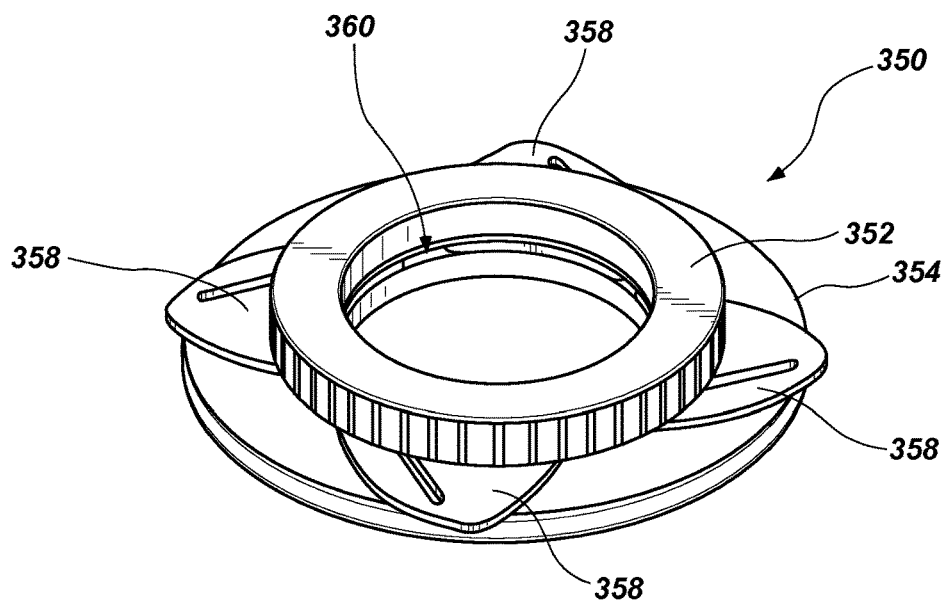

Referring to FIGS. 9A and 9B another suture ring 350 is shown in accordance with an embodiment of the present invention. The suture ring 350 includes a coupling portion 352 and a ring portion 354 such as described above with respect to other embodiments. Additionally, the suture ring 350 includes a valve 356 associated with the coupling portion 302 to enable selective fluid flow through the ring portion 352. As shown, the valve 356 may be configured as a leaflet valve having a plurality of leaflets 358 that slides in a substantially linear direction through slots 360 formed in the coupling portion 352. Again, while not specifically shown, a locking mechanism may also be incorporated to maintain the leaflets 358 in one or more desired positions relative to the coupling portion 352 (e.g., closed, open, partially opened).

Figure 10A:
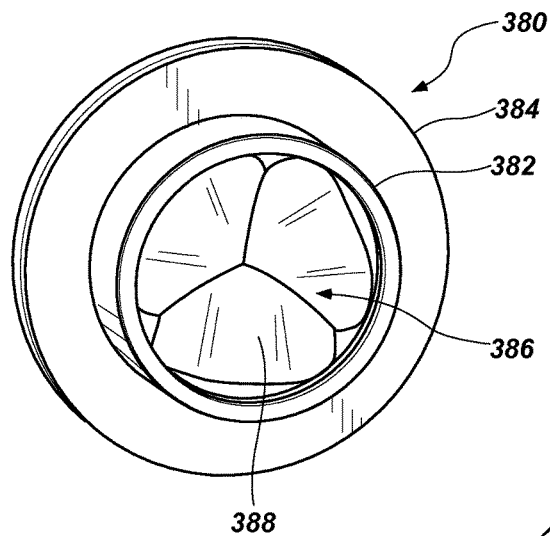
FIGS. 10A-10C show perspective views of a cannula ring in accordance with yet another embodiment of the invention.
Figure 10B:
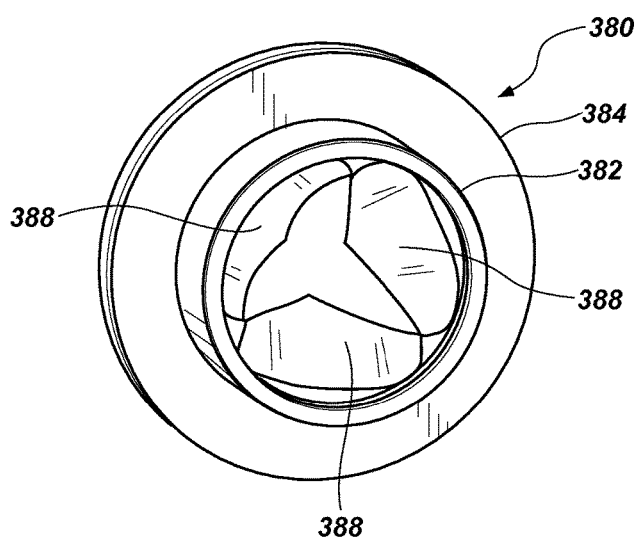
Figure 10C:
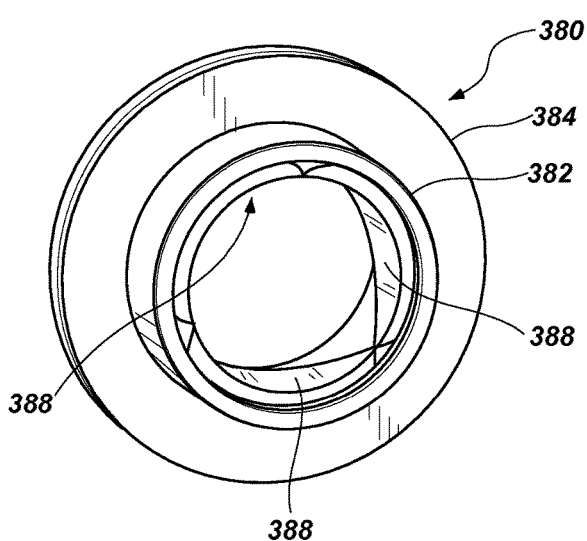

Referring now to FIGS. 10A-10C, another suture ring 380 is shown in accordance with an embodiment of the present invention. The suture ring 380 includes a coupling portion 382 and a ring portion 384 such as described above with respect to other embodiments. Additionally, the suture ring 380 includes a valve 386 associated with the coupling portion 382 to enable selective fluid flow through the ring portion 382. As shown, the valve 386 may be configured as a tricuspid valve with cusps or flaps 388 that are normally in a closed position. Upon application of pressure of a specified magnitude and direction, the flaps will open to enable fluid flow in a single direction. In one embodiment, the flaps may be configured to resist opening based on any negative pressure applied from a distal side of the valve 386, but will open upon application of a stated amount of pressure applied from the proximal side of the valve 386. Again, such a configuration provides substantial flexibility to a practitioner during cannulation procedures and while implanting or adjusting, for example, blood pumps and other associated components.

The various embodiments described herein may be practiced in combination with a variety of know cannulation techniques and components, as well as with various blood pumps and other assist devices. For example, they may be combined with various components, features and techniques as described in U.S. patent application Ser. No. 13/197,605 entitled CONFORMAL CANNULA DEVICE AND RELATED METHODS, filed on Aug. 3, 2011, the disclosure of which is incorporated by reference herein in its entirety.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention includes all modifications, equivalents, and alternatives falling within the spirit and scope of the invention as defined by the following appended claims. Aspects of one described embodiment may be combined with aspects of other embodiments without limitation.

What is claimed is:

1. A cannula ring comprising:
   a body portion including a substantially cylindrical member defining a tubular member having a substantially cylindrical wall defining a lumen wherein at least a portion of the wall is solid; and
   a plurality of anchor arms coupled with the body portion at a coupled end, each of the plurality of anchor arms connecting to the coupled end within a respective one of a plurality of openings, the plurality of anchor arms being configured to be positioned in a first, collapsed state and a second, deployed state, the anchor arms each include a length extending from the coupled end to a free end, wherein the free end is radially displaced from the body portion while in the second, deployed state relative to their positions while in the first, collapsed state;
   wherein the body portion has a constant diameter as the anchor arms move from the first state to the second state; and
   wherein each of the anchor arms, along its length, is adjacent the body portion when in the first state.

2. The cannula ring of claim 1, wherein the anchor arms extend substantially axially along the body portion while in the first, collapsed state.

3. The cannula ring of claim 1, wherein the anchor arms extend substantially circumferentially about the body portion while in the first, collapsed state.

4. The cannula ring of claim 1, wherein the anchor arms are formed of a shape memory material.

5. The cannula ring of claim 1, wherein each anchor arm includes a wire structure.

6. The cannula ring of claim 1, further comprising a coupling structure associated with the body portion.

7. The cannula ring of claim 1, wherein the wall includes a surface feature comprising a textured surface configured to engage abutting tissue.

8. The cannula ring of claim 6, wherein the coupling structure comprises a plurality of threads.

9. The cannula ring of claim 6, wherein the coupling structure comprises a keyed twist-lock structure.

10. The cannula ring of claim 6, wherein the coupling structure comprises a plurality of shoulders configured for use with a ratchet structure.

11. The cannula ring of claim 6, wherein the coupling structure is configured or connection with a compression coupling.

12. The cannula ring of claim 1, further comprising a restraining structure positioned about the anchor arms configured to secure the anchor arms in a first collapsed state.

13. The cannula ring of claim 12, wherein the restraining structure further comprises a band extending circumferentially around the cylindrical member.

14. The cannula ring of claim 13, further comprising a tab formed on the band, wherein pulling the tab breaks the band, thereby freeing the arms to move to a second position.

15. The cannula ring of claim 13, wherein the band is configured to axially slide between a first position and a second position wherein the band secures the anchor arms in a first collapsed state when the band is in a first position, and allows the anchor arms to extend to a second deployed state when the band is slid to a second position.

16. The cannula ring of claim 1, wherein the anchor arms further comprise textured surfaces formed on an exterior surface of the anchor arms.

17. The cannula ring of claim 1 wherein the cylindrical member further comprises an external surface having a circumferential groove, wherein the anchor arms are disposed in the circumferential groove in the first, collapsed state.

* * * * *